(12) United States Patent
Kaplan

(10) Patent No.: US 6,514,193 B2
(45) Date of Patent: Feb. 4, 2003

(54) METHOD OF ADMINISTERING A THERAPEUTICALLY ACTIVE SUBSTANCE

(75) Inventor: Edward J. Kaplan, Boca Raton, FL (US)

(73) Assignee: Microspherix LLC, Boca Raton, FL (US)

( * ) Notice: Subject to any disclaimer, the term of this patent is extended or adjusted under 35 U.S.C. 154(b) by 67 days.

(21) Appl. No.: 09/861,196

(22) Filed: May 18, 2001

(65) Prior Publication Data
US 2002/0058853 A1 May 16, 2002

Related U.S. Application Data

(60) Provisional application No. 60/249,128, filed on Nov. 16, 2000.

(51) Int. Cl.[7] .................. A61M 31/00; A61M 37/00
(52) U.S. Cl. ............................................. 600/7
(58) Field of Search ........................... 600/7, 8

(56) References Cited

U.S. PATENT DOCUMENTS

| | | |
|---|---|---|
| 3,993,073 A | 11/1976 | Zaffaroni |
| 4,167,179 A | 9/1979 | Kirsch |
| 4,351,337 A | 9/1982 | Sidman |
| 4,427,005 A | 1/1984 | Tener |
| 4,697,575 A | 10/1987 | Horowitz |
| 4,700,692 A | 10/1987 | Baumgartner |
| 4,706,652 A | 11/1987 | Horowitz |
| 4,754,745 A | 7/1988 | Horowitz |
| 4,763,642 A | 8/1988 | Horowitz |
| 4,815,449 A | 3/1989 | Horowitz |
| 4,820,844 A | 4/1989 | Kagiya et al. |
| 5,030,195 A | 7/1991 | Nardi |
| 5,059,166 A | 10/1991 | Fischell et al. |
| 5,242,373 A | 9/1993 | Scott et al. |
| 5,342,283 A | 8/1994 | Good |
| 5,424,288 A | 6/1995 | Order |
| 5,460,592 A | 10/1995 | Langton et al. |

(List continued on next page.)

FOREIGN PATENT DOCUMENTS

| | | |
|---|---|---|
| WO | WO 96/14880 | 5/1996 |
| WO | WO 97/19706 | 6/1997 |

OTHER PUBLICATIONS

Philippe et al., "Local and Sustained Delivery of 5–Fluorouracil from Biodegradable Microspheres for the Radiosensitization of Glioblastoma," Cancer, 86: 325, 1999.

(List continued on next page.)

Primary Examiner—Paul J. Hirsch
(74) Attorney, Agent, or Firm—Holland & Knight LLP

(57) ABSTRACT

A method for administering a therapeutically active component including a non-radioactive drug to a target tissue in a subject includes the steps of: (a) providing a brachytherapy seed having a size and shape suitable for passing through the bore of a needle having an interior diameter of less than about 2.7 millimeters (10 gauge); (b) providing a brachytherapy implantation instrument comprising at least one brachytherapy implantation needle having a bore having an interior diameter of less than about 2.7 millimeters (10 gauge), and being adapted to accept the brachytherapy seed into the bore of the at least one brachytherapy implantation needle and deliver the accepted implantation device into a target tissue; (c) introducing the brachytherapy seed into the bore of the at least one implantation needle of the brachytherapy implantation instrument; (d) introducing at least a portion of the at least one brachytherapy implantation needle into a target tissue in the subject; and (e) actuating the brachytherapy implantation instrument such that the brachytherapy seed is delivered through the bore of the brachytherapy implantation needle into the target tissue.

8 Claims, 5 Drawing Sheets

U.S. PATENT DOCUMENTS

| | | | |
|---|---|---|---|
| 5,486,360 A | | 1/1996 | Ballagh et al. |
| 5,538,726 A | | 7/1996 | Order |
| 5,595,979 A | | 1/1997 | Snyder |
| 5,620,700 A | | 4/1997 | Berggren et al. |
| 5,626,829 A | | 5/1997 | Koutrouvelis |
| 5,626,862 A | | 5/1997 | Brem et al. |
| 5,650,442 A | | 7/1997 | Mitchell et al. |
| 5,871,437 A | | 2/1999 | Alt |
| 6,102,844 A | * | 8/2000 | Ravins .......................... 600/8 |
| 6,132,359 A | * | 10/2000 | Bolebaugh ..................... 600/8 |
| 6,159,143 A | | 12/2000 | Lennox |
| 6,241,962 B1 | | 6/2001 | Nicolini et al. |
| 6,248,057 B1 | | 6/2001 | Mavity et al. |

OTHER PUBLICATIONS

Wei et al., "Carboplatin–Loaded PLGA Microspheres for Intracerebral Implantation: In Vivo Characterization," Drug Delivery, 4: 301, 1997.

Kharkevich et al., "Employment of magnet–susceptible microparticles for the targeting of drugs," J. Pharm. Pharmacol., 41: 286, 1989.

Gobin et al., "Embolization with Radiopaque Microbeads of Polyacrylonitrile Hydrogel: Evaluation in Swine[1]," Radiology, 214: 113, 2000.

Mauer et al., "Hepatic artery embolisation with a novel radiopaque polymer causes extended liver necrosis in pigs due to occlusion of the concomitant portal vein,"Journal of Hepatology , 32: 261, 2000.

Yang et al., "Diagnostic and Therapeutic Potential of Poly-(benzyl L–glutamate)," Journal of Pharmaceutical Sciences, 83: 328, 1994.

Benzina et al., "Studies on a new radiopaque polymeric biomaterial," Biomaterials, 15: 1122, 1994.

Hafeli et al., "Effective Targeting of Magnetic Radioactive $^{90}$Y–microspheres to Tumor Cells by an Externally Applied Magnetic Field. Preliminary In Vitro and In Vivo Results," Nuclear Med. Biol., 22: 147, 1995.

Thanoo et al., "Tantalum–loaded polyurethane microspheres for particulate embolization: preparation and properties," Biomaterials, 12: 525, 1991.

Horak et al., "New radiopaque polyHEMA–based hydrogel particles," Journal of Biomedical Materials Research, 34: 183, 1997.

Li et al., "Biodistribution of Cyclic Carbonate of Ioxilan: A Radiopaque particulate Macrophage Imaging Agent," Acad. Radiol, 3: 500, 1996.

Wang et al., "Intratumoral Injection of Rhenium–188 Microspheres into an Animal Model of Hepatoma," The Journal of Nuclear Medicine, 39:1752, 1998.

Wunderlich et al., "Preparation and biodistribution of rhenium–188 labeled albumin microspheres B 20: a promising new agent for radiotherapy," Applied Radiation and Isotopes, 52: 63, 2000.

Lester et al., "Assessment of Barium Impregnated Polyethylene Spheres (BIPs®) as a Measure of Solid–Phase Gastric Emptying in Normal Dogs–Comparision to Scintigraphy," Veterinary Radiology & Ultrasound, 40: 465, 1999.

Thanoo, B. and A. Jayakrishnan, "Radiopaque hydrogel microspheres," J. Microencapsulation, 6: 233, 1989.

Leibel, S. and T. Phillips, "Textbook of Radiation Oncology," 1998.

Perez, C. and L. Brady, "Principles and Practice of Radiation Oncology," Third Edition: 54, 1998.

Ramirez et al., "Biodegradable poly(DL–lactic–co–glycolic acid) microspheres containing tetracaine hydrochloride. In–vitro release profile," J. Microencapsulation, 16: 105, 1999.

Miyamoto et al., "Biodegradable scleral implant for intravitreal controlled release of fluconazole," Current Eye Research, 16: 930, 1997.

Kuriakose et al., "Interleukin–12 Delivered by Biodegradable Microspheres Promotes the Antitumor Activity of Human Peripheral Blood Lymphocytes in a Human Head and Neck Tumor Xenograft/Scid Mouse Model," Head & Neck, 57, 2000.

Kubek et al., "Prolonged seizure suppression by a single implantable polymeric–TRH microdisk preparation," Brain Research, 809: 189, 1998.

Kong et al., "Intralesionally Implanted Cisplatin Plus Systemic Carmustine for the Treatment of Brain Tumor in Rats," Journal of Surgical Oncology, 69: 76, 1998.

Walter et al., "Interstitial Taxol Delivered from a Biodegradable Polymer Implant against Experimental Malignant Glioma[1]," Cancer Research, 54: 2207, 1994.

Laurencin et al., "Bioerodible Polyanhydrides for Antibiotic Drug Delivery: In Vivo Osteomyelitis Treatment in a Rat Model System," Journal of Orthopaedic Research, 11: 256, 1993.

Tamargo et al., "Interstitial Chemotherapy of the 9L Gliosarcoma: Controlled Release Polymers for Drug Delivery in the Brain[1]," Cancer Res., 53: 329, 1993.

Fung et al., "Pharmacokinetics in Interstitial Delivery of Carmustine, 4–Hydroperoxycyclophosphamide, and Paclitaxel from a Biodegradable Polymer Implant in the Monkey Brain[1], " Cancer Research 58: 672, 1998.

Judy et al., "Effectiveness of controlled release of a cyclophosphamide derivative with polymers against rat gliomas," J. Neurosurg, 82: 481, 1995.

Brem et al., "Interstitial chemotherapy with drug polymer implants for the treatment of recurrent–gliomas," J. Neurosurg 74: 441, 1991.

Park et al., "Biodegradable polyanhydride devices of cefazolin sodium, bupivacaine, and taxol for local drug delivery: preparation, and kinetics and mechanism of in vitro release," Journal of Controlled Release, 52: 179, 1998.

Conforti et al., "Anti–inflammatory Activity of Polyphosphazene–based Naproxen Slow–release Systems," J. Pharm. Pharmacol, 48: 468, 1996.

Straw et al., "Effects of Cis–Diammindeichloroplatinum II Released from D,L–Polylactic Acid Implanted Adjacent to Cortical Allografts in Dogs," Journal of Orthopaedic Research, 12: 871, 1994.

Ringkjob, R., "Treatment of Intracranial Gliomas and Metastatic Carcinomas by Local Application of Cytostatic Agents," Aeta Neurol. Scandinav, 44: 318, 1968.

Grossman et al., "The Intracerebral distribution of BCNU delivered by surgically implanted biodegradable polymers," J. Nuerosurg, 76: 640, 1992.

Chattaraj et al., "Biodegradable microparticles of influenza viral vaccine: comparison of the effects of routes of administration on the in vivo immune response in mice," Journal of Controlled Release, 58: 223, 1999.

Yoshida et al., "In vivo release of cisplatin from a needle–type copolymer formulation implanted in rat kidney," Biomaterials, 10:, 17, 1989.

Cardinale et al., "Effect of Interstitial and/or Systemic Delivery of Tirapazamine on the Radiosensitivity of Human Glioblastoma Multiforme in Nude Mice," Radiation Oncology Investigations, 6: 63, 1998.

Valtonen et al., "Interstitial Chemotherpy with Carmustine–loaded Polymers for High–grade Gliomas: A Randomized Double–blind Study," Neurosurgery, 41: 44, 1997.

Yuan et al., "Implantable Polymers for Tirapazamine Treatments of Experimental Intracranial Malignant Glioma," Radiation Oncology Investigation, 7: 218, 1999.

Ewend et al., "Local Delivery of Chemotherapy and Concurrent External Beam Radiotherapy Prolongs Survival in Metastatic Brain Tumor Models[1]," Research, 56: 5217, 1996.

Yapp et al., "Tumor Treatment by Sustained Intratumoral Release of Cisplatin: Effects of Drug Alone and Combined with Radiationl" 39:497, 1997.

Yapp et al., "The Potentiation of the Effect of Radiation Treatment by Intratumoral Delivery of Cisplatin," Int. J. Radiation Oncology Biol. Phys., 42: 413, 1998.

Yapp et al., "Radiosensitization of a mouse tumor model by sustained intra–tumoral release of Etanidazole and Tirapazamine using a biodegradable polymer implant device," Radiotherapy and Oncology, 53: 77, 1999.

Brem et al., "Placebo–controlled trail of safety and efficacy of intraoperative controlled delivery by biodegradable polymers of chemotherapy for recurrent gliomas," Lancet, 345: 1008, 1995.

Brem et al., "Biodegradable polymers for controlled delivery of chemotherapy with and without radiation therapy in the moneky brain," J. Neurosurg., 80: 283, 1994.

Dash, A. and G. Cudworth II, "Therapeutic Applications of Implantable Drug Delivery Systems," JPM, 40: 1, 1998.

Harper et al., "Enhanced Efficacy of a Novel Controlled Release Paclitaxel Formulation (PACLIMER Delivery System) for Local–Regional Therapy of Lung Cancer Tumor Nodules in Mice[1]," Clinical Cancer Research, 5: 4242, 1999.

Yapp et al., "Cisplatin delivery by biodegradable polymer implant is superior to systemic delivery by osmotic pump or i.p. injection in tumor–bearing mice," Anti–Cancer Drugs, 9: 791, 1998.

Fowler et al., "Evaluation of an Implant that Delivers Leuprolide for 1 Year for the Palliative Treatment of Prostate Cancer," Urology, 55: 639, 2000.

Camarata et al., "Sustained release of nerve growth factor from biodegradable polymer microspheres," Neurosurgery, 30: 313, 1992.

Chen et al., "Carboplatin–loaded PLGA microspheres for intracerebral implantation: in vivo characterization," Drug Delivery, 4: 301, 1997.

Domb et al., "Polyanhydride: I Preparation of high molecular weight polymers," J Polym. Sci., 25: 3373, 1987.

During et al., "Controlled release of dopamine from a polymeric brain implant: in vivo characterization," Ann. Neurology, 25: 351, 1989.

Menei et al., "Local and sustained delivery of 5–fluorouracil from biodegradable microspheres for the radiosensitization of glioblastoma," Cancer, 86: 325, 1999.

Moritera et al., "Biodegradable microspheres containing adriamycin in the treatment of proliferative vitreoretinopathy," Invest Ophthalmol Vis Sci, 33: 3125, 1992.

Tamargo et al., "Growth inhibition of the 9L glioma using polymers to release heparin and cortisone acetate," J Neurooncol, 9: 131, 1990.

Tamargo et al., "Interstitial delivery of dexamethasone in the brain for the reduction of peritumoral edema," J Neurosurg, 74: 956, 1991.

Weingart et al., "Local delivery of the topoisomerase I inhibitor camptothecin prolongs survival in the rat intracranial 9L gliosarcoma model," Int J Cancer, 62: 1, 1995.

Williams et al., "Synthetic, implantable polymers for local delivery of IUDR to experimental human malignant glioma," IJROBP, 42: 631, 1998.

Qian et al., "Fabrication and characterization of controlled release poly($_{D,L}$–lactide–co–glycolide) millirods," J. Biomed Mater Res., 55: 512, 2001.

Beer et al., "Extended release if adenovirus from polymer microspheres: potential use in gene therapy for brain tumors," Advanced Drug Delivery Reviews, 27: 59, 1997.

Kunou et al., "Controlled intraocular delivery of ganciclovir with use of biodegradable scleral implant in rabbits," Journal of Controlled Release, 37: 143, 1995.

Reinhard et al., "Polymeric controlled release of dexamethasone in normal rat brain," Journal of Controlled Release, 16: 331, 1991.

Sanchez et al., "In Vivo Study of the Tissue Distribution and Immunosuppressive Response of Cyclosporin A–Loaded Polyester Micro–and Nanospheres," Drug Delivery, 2: 21, 1995.

Alonso et al., "Biodegradable microspheres as controlled–release tetanus toxoid delivery systems," Vaccine, 12: 299, 1994.

* cited by examiner

METHOD OF ADMINISTERING A THERAPEUTICALLY ACTIVE SUBSTANCE

CROSS REFERENCE TO RELATED APPLICATIONS

The present application claims the priority of U.S. provisional application No. 60/249,128 filed Nov. 16, 2000.

STATEMENT AS TO FEDERALLY SPONSORED RESEARCH

Not applicable.

FIELD OF THE INVENTION

The invention relates generally to the fields of medicine and delivery of therapeutically active substances. More particularly, the invention relates to implantable brachytherapy devices.

BACKGROUND

Radioactive seed therapy, commonly referred to as brachytherapy, is an established technique for treating various medical conditions, most notably prostate cancer. In a typical application of brachytherapy for treating prostate cancer, about 50–150 small seeds containing a radioisotope that emits a relatively short-acting type of radiation are surgically implanted in the diseased tissue. Because the seeds are localized near the diseased tissue, the radiation they emit is thereby concentrated on the cancerous cells and not on distantly located healthy tissue. In this respect, brachytherapy is advantageous over conventional external beam radiation.

A number of devices have been employed to implant radioactive seeds into tissues. See, e.g., U.S. Pat. No. 2,269,963 to Wappler; U.S. Pat. No. 4,402,308 to Scott; U.S. Pat. No. 5,860,909 to Mick; and U.S. Pat. No. 6,007,474 to Rydell. In a typical protocol for treating prostate cancer, an implantation device having a specialized needle is inserted through the skin between the rectum and scrotum into the prostate to deliver radioactive seeds to the prostate. The needle can be repositioned or a new needle used for other sites in the prostate where seeds are to be implanted. Typically, 20–40 needles are used to deliver between about 50–150 seeds per prostate. A rectal ultrasound probe is used to track the position of the needles. Once the end of a given needle is positioned in a desired location, a seed is forced down the bore of the needle so that it becomes lodged at that location.

As the seeds are implanted in the prostate as desired, the needles are removed from the patient. Over the ensuing several months the radiation emitted from the seeds kills the cancerous cells. Surgical removal of the seeds is usually not necessary because the type of radioisotope generally used decays over the several month period so that very little radiation is emitted from the seeds after this time.

Currently marketed radioactive seeds take the form of a capsule encapsulating a radioisotope. See, e.g., Symmetra® I-125 (Bebig GmbH, Germany); Iogold™ I-125 and Iogold™ Pd-103 (North American Scientific, Inc., Chatsworth, Calif.); Best® I-125 and Best® Pd-103 (Best Industries, Springfield, Va.); Brachyseed® I-125 (Draximage, Inc., Canada); Intersource® Pd-103 (International Brachytherapy, Belgium); Oncoseed® I-125 (Nycomed Amersham, UK); STM 1250 I-125 (Sourcetech Medical, Carol Stream, Ill.); Pharmaseed® I-125 (Syncor, Woodland Hills, Calif.); Prostaseed™ I-125 (Urocor, Oklahoma City, Okla.); and I-plant® I-125 (Implant Sciences Corpation, Wakefield, Mass.). The capsule of these seeds is made of a biocompatible substance such as titanium or stainless steel, and is tightly sealed to prevent leaching of the radioisotope. The capsule is sized to fit down the bore of one of the needles used in the implantation device. Since most such needles are about 18 gauge, the capsule typically has a diameter of about 0.8 mm and a length of about 4.5 mm.

The two radioisotopes most commonly used in prostate brachytherapy seeds are iodine (I-125) and palladium (Pd-103). Both emit low energy irradiation and have half-life characteristics ideal for treating tumors. For example, I-125 seeds decay at a rate of 50% every 60 days, so that using typical starting doses their radioactivity is almost exhausted after ten months. Pd-103 seeds decay even more quickly, losing half their energy every 17 days so that they are nearly inert after only 3 months.

Radioactive brachytherapy seeds may also contain other components. For example, to assist in tracking their proper placement using standard X-ray imaging techniques, such seeds may contain a radiopaque marker. Markers are typically made of high atomic number (i.e., "high Z") elements or alloys or mixtures containing such elements. Examples of these include platinum, iridium, rhenium, gold, tantalum, lead, bismuth alloys, indium alloys, solder or other alloys with low melting points, tungsten, and silver. Many radiopaque markers are currently being marketed including: platinum/iridium markers (Draximage, Inc. and International Brachytherapy), gold rods (Bebig GmbH), gold/copper alloy markers (North American Scientific), palladium rods (Syncor), tungsten markers (Best Industries), silver rods (Nycomed Amersham), silver spheres (International Isotopes Inc. and Urocor), and silver wire (Implant Sciences Corp.). Other radiopaque markers include polymers impregnated with various substances (see, e.g., U.S. Pat. No. 6,077,880).

A number of different U.S. patents disclose technology relating to brachytherapy. For example, U.S. Pat. No. 3,351,049 to Lawrence discloses the use of a low-energy X-ray-emitting interstitial implant as a brachytherapy source. In addition, U.S. Pat. No. 4,323,055 to Kubiatowicz; U.S. Pat. No. 4,702,228 to Russell; U.S. Pat. No. 4,891,165 to Suthanthiran; U.S. Pat. No. 5,405,309 to Carden; U.S. Pat. No. 5,713,828 to Coniglione; U.S. Pat. No. 5,997,463 to Cutrer; U.S. Pat. No. 6,066,083 to Slater; and U.S. Pat. No. 6,074,337 to Tucker disclose technologies relating to brachytherapy devices.

SUMMARY

The invention relates to a brachytherapy seed that includes a drug or other therapeutically active substance that can be delivered to a subject upon implantation into the subject through the bore of a brachytherapy implantation needle. Because the brachytherapy seeds of the invention can be sized and shaped to fit through the bore of a brachytherapy implantation needle, they are suitable for use with brachytherapy seed implantation instruments such as an implant needle, a Henschke, Scott, or Mick applicator, or a like device such as a Royal Marsden gold grain gun. A drug or other therapeutically active substance can be included in the seed in addition to, or as an alternative to, a radioisotope. A drug or other therapeutically active substance can also be associated with a biodegradable component so that its rate of release in the implantation site can be controlled according to the rate that the biodegradable substance decomposes at the implantation site. Thus, like conventional radioactive brachytherapy seeds, the seeds within the invention can be precisely implanted in many different target tissues without the need for invasive surgery. And similar to the radiation emitted from conventional brachytherapy seeds, the therapeutically active substance included within a seed of the invention can be delivered in a controlled fashion over a relatively long period of time (e.g., weeks, months, or longer periods). Moreover, because concentrations of the therapeutically active substance will be greater at the implantation site (e.g., the diseased tissue), any potential deleterious effect of the therapeutically active substance on healthy tissue located away from the implantation site will be reduced.

Depending on the particular application, the brachytherapy seeds of the present invention offer other advantages. Among these, for example, compared to conventional systemic administration (e.g., oral or intravenous delivery) of therapeutically active substances, the brachytherapy seeds of the invention can provide higher and more consistent concentrations of a therapeutically active substance to a target tissue. They can also eliminate the need for repeated injections as well as circumvent delivery problems such as where a target tissue lacks an intact vascular supply (e.g., a target tissue whose blood flow may be compromised) or is otherwise sequestered from the blood supply (e.g., via the blood-brain barrier of the central nervous system). In some versions of the seeds of the invention that do not contain a radioisotope (e.g., those having only the therapeutically active substance and biodegradable component), after the therapeutically active substance is completely released and the biodegradable component is fully decomposed, no foreign device will remain at the implantation site.

Accordingly, the invention features methods for administering a therapeutically active component to a target tissue in a subject. One such method includes the steps of: providing a brachytherapy seed including a biocompatible component, a therapeutically active component including a non-radioactive drug, and a radiopaque marker, the biocompatible component being (a) physically associated with a therapeutically active component and (b) in contact with the radiopaque marker, wherein the brachytherapy seed has a size and shape suitable for passing through the bore of a needle having an interior diameter of less than about 2.7 millimeters (10 gauge); providing a brachytherapy implantation instrument including at least one brachytherapy implantation needle having a bore having an interior diameter of less than about 2.7 millimeters (10 gauge), and being adapted to accept the brachytherapy seed into the bore of the at least one brachytherapy implantation needle and deliver the accepted implantation device into a target tissue; introducing the brachytherapy seed into the bore of the at least one needle of the brachytherapy implantation instrument; introducing at least a portion of the at least one brachytherapy implantation needle into a target tissue in the subject; and actuating the brachytherapy implantation instrument such that the brachytherapy seed is delivered through the bore of the brachytherapy implantation needle into the target tissue.

Another method within the invention for administering a therapeutically active component to a target tissue in a subject includes the steps of: providing a brachytherapy seed including a sealed container, and a non-metal biocompatible component, and a therapeutically active component including a non-radioactive drug, the biocompatible component being physically associated with the therapeutically active component to form a combination product; and the sealed container being made of a non-biodegradable substance, housing a radioisotope, and being at least partially coated with the combination product, wherein the brachytherapy seed having a size and shape suitable for passing through the bore of a needle having an interior diameter of less than about 2.7 millimeters (10 gauge); providing a brachytherapy implantation instrument including at least one brachytherapy implantation needle having a bore having an interior diameter of less than about 2.7 millimeters (10 gauge), and being adapted to accept the brachytherapy seed into the bore of the at least one brachytherapy implantation needle and deliver the accepted implantation device into a target tissue; introducing the brachytherapy seed into the bore of the at least one needle of the brachytherapy implantation instrument; introducing at least a portion of the at least one brachytherapy implantation needle into a target tissue in the subject; and actuating the brachytherapy implantation instrument such that the brachytherapy seed is delivered through the bore of the brachytherapy implantation needle into the target tissue.

In the foregoing methods, the biocompatible component can be biodegradable and include a polymer such as poly (bis(p-carboxyphenoxy) propane anhydride); poly(bis(p-carboxy) methane anhydride); poly(D,L-lactic-coglycolic acid); poly(isobutylcyanoacrylate); a copolymer of polycarboxyphenoxypropane and sebacic acid; open cell polylactic acid; a co-polymer of a poly-fatty acid dimer and sebacic acid; poly(carboxyphenoxy) hexane; poly-1,4-phenylene dipropionic acid; polyisophthalic acid; polydodecanedioic acid; or other polymers described below.

The therapeutically active component can include a drug such as stimulating and growth factors; gene vectors; viral vectors; anti-angiogenesis agents; cytostatic, cytotoxic, and cytocidal agents; transforming agents; apoptosis-inducing agents; radiosensitizers; radioprotectants; hormones; enzymes; antibiotics; antiviral agents; mitogens; cytokines; anti-inflammatory agents; immunotoxins; antibodies; or antigens. For example, the drug can be an anti-neoplastic agent such as paclitaxel, 5-fluorouracil, or cisplatin. It can also be a radiosensitizing agent such as 5-fluorouracil, etanidazole, tirapazamine, BUdR, or IUdR.

The radiopaque marker can include platinum, iridium, rhenium, gold, tantalum, bismuth, indium, tungsten, silver, or a radiopaque polymer. Radioisotopes for use in the invention can include $^{125}$I and $^{103}$Pd.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

Figure 1:
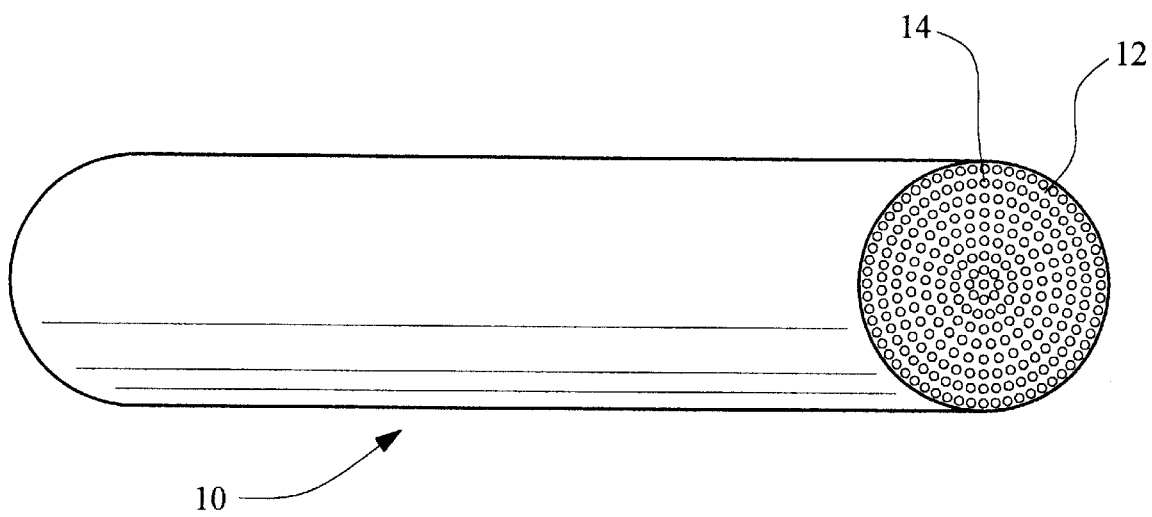
FIG. 1 is a schematic side view of a cylindrically shaped brachytherapy seed of the invention.

The invention encompasses compositions and methods relating to implantable brachytherapy seeds including a biocompatible component associated with a therapeutically active substance. Referring to the drawings there are illustrated various different embodiments of the brachytherapy seeds of the invention. In FIG. 1, there is shown a brachytherapy seed 10 composed of a biocompatible component 12 associated with a therapeutically active component 14 (schematically shown as small circles or spheres). As illustrated, the therapeutically active component 14 is present as a plurality of small particles dispersed throughout a matrix consisting of the biocompatible component 12. The mixture of the components 12 and 14 is formed into the cylindrically shaped brachytherapy seed 10.

The brachytherapy seed 10 shown in FIG. 1 has a size and shape suitable for passing through the bore of a brachytherapy implantation needle. Although the bore can be any size compatible with brachytherapy methods, in order to minimize damage to tissue, the bore preferably has an interior diameter of between about 0.01 and 10 mm (e.g., 0.009, 0.01, 0.02, 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 4, 5, 6, 7, 8, 9, 10, or 11 mm). For use with 10 gauge or less brachytherapy implantation needles, seed 10 has a size and shape that can pass through a bore having a diameter of less than about 2.7 millimeters (i.e., the interior diameter of a standard 10 gauge brachytherapy implantation needle). For smaller needles such as 15 and 18 gauge needles, seed 10 has a size and shape that can pass through bores having an interior diameter of less than about 1.4 millimeters (e.g., 1.40, 1.39, 1.38, 1.37, 1.36, 1.35, or 1.34 mm) or less than about 0.84 millimeters (e.g., 0.86, 0.85, 0.84, 0.83, 0.82, 0.81, 0.80 mm), respectively.

Although there is no lower limit as to how small any dimension of seed 10 can be, in many applications, those that are not able to pass through bores smaller than 0.3 mm are preferred. For example, in many applications where it is desirable for the implanted brachytherapy seeds to maintain their orientation in the tissue, the seed 10 should be large enough to stayed lodged at the site of implantation in the desired orientation for a relatively long period, larger seeds are preferred. In some cases, the selection of materials for use in the seed 10 will effect its size. For instance, in versions of the seed 10 where the biocompatible component 12 is a stainless steel or titanium capsule, the walls of the capsule may need to be greater than a certain minimum size in order to maintain the structural integrity of the seed 10. In addition, in some applications, the seed 10 should also be large enough to carry a sufficient amount of the therapeutically active component 14 to be therapeutically active (i.e., a therapeutically effective amount or an amount that exerts a desired medically beneficial effect). In order facilitate the passage of seed 10 through the bore of a needle while preventing jamming of the brachytherapy implantation needle bore (e.g., caused by clumping of several seeds), it is also preferred that the diameter of seed 10 be just slightly less than the diameter of the bore of the needle (e.g., 0.5–5% less).

For use with the needles used in many conventional brachytherapy seed implantation devices, brachytherapy seeds shaped into a cylinder (or rod) having a diameter of between about 0.8 to 3 millimeters (e.g., 0.7, 0.8, 0.9, 1, 1.1, 1.2, 1.3, 1.4, 1.5, 1.6, 1.7, 1.8, 1.9, 2, 2.1, 2.1, 2.2, 2.3, 2.4, 2.5, 2.6, 2.7, 2.8, 2.9, 3.0, or 3.1 mm) and a length of between about 4 to 10 millimeters (e.g., 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, or 6.1 mm) are preferred. Because many conventional brachytherapy seed applicators make use of brachytherapy implantation needles about 17 to 18 gauge in size, cylindrically shaped brachytherapy seeds having a diameter of between about 0.8 and 1.1 mm (e.g, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.01, 1.02, 1.03, 1.04, 1.05, 1.06, 1.07, 1.08, 1.09, 1.1, and 1.11 mm) and a length greater than the diameter (e.g., 2–10 mm) are preferred for use with such applicators. In particular, because many conventional brachytherapy seed applicators are designed to accept conventional radioactive brachytherapy seeds that have a diameter of about 0.8 millimeters and a length of about 4.5 millimeters, brachytherapy seeds within the invention of similar size are especially preferred.

Figure 2:
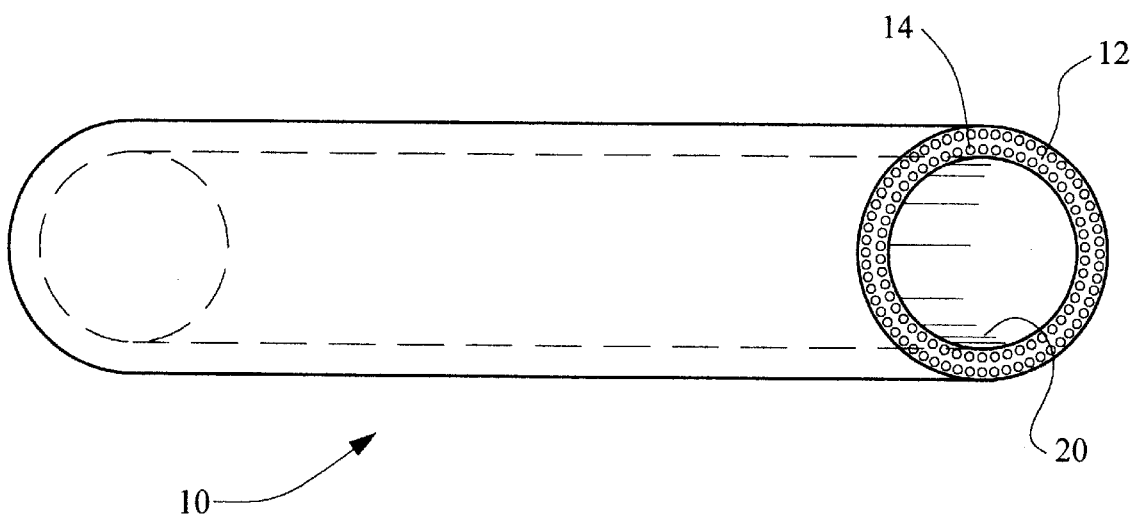
FIG. 2 is a schematic side view of a hollow tube-shaped brachytherapy seed of the invention.

Brachytherapy seeds within the invention are also not limited to those being cylindrical in shape (e.g., seed 10 shown in FIG. 1), but rather can be any shape suitable for passing through the bore of a needle. For example, in many cases, seeds within the invention can be cuboid, spheroid, ovoid, ellipsoid, irregularly shaped, etc. The ends of the seeds can be rounded, squared, tapered, conical, convex, concave, scalloped, angular, or otherwise-shaped. The brachytherapy seeds within the invention can be solid as shown in FIG. 1, but can also have one or more cavities or pores (e.g., to increase the surface area of the seed exposed to the target tissue). As one example, as illustrated in FIG. 2, a brachytherapy seed 10 of the invention is shaped into a hollow tube 18 having a cylindrical cavity 20. In preferred versions of seed 10, cylindrical cavity 20 is sized to accept and envelop a standard-sized brachytherapy seed (e.g., one having a diameter of about 0.8 mm and a length of about 4.5 mm). For use, the seed 10 can be placed over the standard-sized brachytherapy seed, and introduced into the bore of a needle (sized to accept the enveloped seed) for implantation into a target tissue. The seed 10 shown in FIG. 2 can also be used alone without being placed over a standard-sized brachytherapy seed, e.g., to increase the surface area exposed in the site of implantation. Hollow tube 18 can have any wall thickness or length suitable for wholly or partially enveloping a standard-sized brachytherapy seed and passing through the bore of a needle. Preferably it has a wall thickness between about 0.01 and 0.1 mm (e.g., 0.01, 0.02, 0.03, 0.04, 0.05, 0.06, 0.07, 0.08, 0.09, 0.1 mm) and a length of between about 1 to 4.5 mm (e.g., 1, 1.5, 2, 2.5, 3, 3.5, 4, and 4.5 mm).

Referring again to FIGS. 1 and 2, biocompatible component 12 can be composed of any material suitable for implantation in a target tissue in an animal subject (e.g., a mammal such as a human patient) that can be associated with therapeutically active component 14 such that all or part of the therapeutically active component 14 will be delivered to the target tissue when the brachytherapy seed 10 is introduced into the implantation site. A number of materials suitable for use a component 12 are known. See, e.g., Biomaterials Engineering and Devices: Human Applications: Fundamentals and Vascular and Carrier Applications, Donald L. Wise et al. (eds), Humana Press, 2000; Biomaterials Science: An Introduction to Materials in Medicine, Buddy D. Ratner et al. (eds.), Academic Press, 1997; and Biomaterials and Bioengineering Handbook, Donald L. Wise, Marcel Dekker, 2000.

As a representative example, the biocompatible component 12 can be made of a substance other than metal (i.e., a non-metal biocompatible component). An exemplary non-metal biocompatible component is a biodegradable polymer that can act as a carrier for the therapeutically active component 14. Numerous such polymers are known including, e.g., polyorthoesters, polyanhydrides, polylactides (PLA), polyglycolides (PGA), and poly(lactide-co-glycolides) (PLGA). Other suitable biodegradable polymers include: polylactic acid, polyglycolic acid,poly L-lactide-co-glycolide, polydioxanone, poly glycolide-co-trimethylene carbonate, poly ethylene carbonate, polyiminocarbonates, polyhydroxybutyrate, polyesteramides, and polyamino acids. More specific examples of suitable biodegradable polymers include: poly[bis(p-carboxyphenoxy) propane anhydride] (PCPP); poly[bis(p-carboxy) methane anhydride (PCPM); Resomer® [Poly(D, L-lactic-coglycolic acid) (PLAGA)]; poly (isobutylcyanoacrylate) (PIBCA); Biodel®, a copolymer of poly-carboxyphenoxypropane and sebacic acid (PCPP:SA); OPLA® (open cell polylactic acid); poly-fatty acid dimer and sebacic acid [P(FAD-SA)]; poly(carboxyphenoxy) hexane (PCPH); poly-1,4-phenylene dipropionic acid (PPDP); polyisophthalic acid [P(Iph-SA)]; and polydodecanedioic acid (PDD). Other polymers suitable for use as component 12 include: polyamido—amines (PAA), poly-2-hydroxy ethyl methacrylate, poly N-vinyl pyrrolidone, polymethyl methacrylate, polyvinyl alcohol, polyacrylic acid, polyacrylamide, polyethylene-co-vinyl acetate, polyethylene glycol, polymethacrylic acid, and those described in U.S. Patent Nos. 3,625,214; 3,867,519; 4,093,709; 4,391,797; and 4,767,628.

The invention is not limited to the use of any particular substance for use as the biocompatible component 12. Rather certain substances will be preferred for certain applications while others will be preferred for other applications. A skilled artisan can select the particular composition of the component 12 that is most suited for a given application. For example, where the seed 10 is intended to be used to slowly deliver the therapeutically active component 14 when implanted in a target tissue, a biocompatible and biodegradable material made up of a chemical composition of a polymer known to degrade at a desired rate when placed under conditions similar to those encountered in the implantation site can be selected for use as component 12. Various characteristics of such biodegradable components are described, e.g., in Biomaterials Engineering and Devices: Human Applications : Fundamentals and Vascular and Carrier Applications; Biomaterials Science : An Introduction to Materials in Medicine; and Biomaterials and Bioengineering Handbook, supra. For example, by selecting an appropriate material for use as the biocompatible component 12 of the brachytherapy seed 10, the duration of release of the therapeutically active component 14 from seed 10 can be varied from less than about an hour to more than about several months (e.g., 10 min., 30 min., 1 h., 2 h., 3 h., 6 h., 12 h., 1 day, 2 days, 3 days, 1 week, 2 weeks, 1 month, 2 months, 3 months, 4 months, 5 months, 6 months, 1 year, 2 years, or 3 years). Biocompatible component 12 is not limited to being biodegradable. For example, component 12 can also be made of a non-biodegradable material such as stainless steel or titanium. In this case, biocompatible component 12 can be coated or otherwise associated with therapeutically active component 14, such that component 14 will be delivered to a target tissue into which seed 10 is implanted. For instance, component 12 might take the form of a porous stainless steel or titanium cylinder having a plurality of pores through its outer surface, such pores being filled with or otherwise in communication with the component 14 such that the component 14 can diffuse from the seed 10 into the environment surrounding the seed 10 (e.g., a target tissue).

Compositions with unknown or incompletely investigated characteristics might also be used as biocompatible component 12. These can be tested for suitability in a given application by conventional clinical testing. For example, a test composition can be fashioned into a brachytherapy seed and implanted in a laboratory animal in a selected target tissue. The effects of the implanted compositions on the animal can then be monitored over a period of time. Those that prove to be biocompatible (e.g., not causing an undesired response such as calcification or an allergic response) and have a desired rate of degradation and delivery of a therapeutically active component (if included in the test seed) can thus be identified.

Therapeutically active component 14 is a material that can (a) be implanted in a target tissue of an animal subject (e.g., a mammal such as a human patient) to exert an effect on the animal's physiology, and (b) be associated with the biocompatible component 12 in the brachytherapy seed 10. Myriad different substances can be used as the therapeutically active component 14. See, e.g., Physician's Desk Reference, The Merck Index, and USP DI® 2000 published by U.S. Pharmacopeia. For example, the therapeutically active component 14 can include a small molecule drug (e.g., a non-peptide or non-nucleic acid-based molecule with a molecular weight generally less than 5 kDa) such as a chemical with known anti-cancer properties. It can also include a drug in the form of a biologic such as a polypeptide (e.g., an antibody or a cytokine) or nucleic acid (e.g., an expression vector). Further examples as to the form that the drug can take include without limitation: stimulating and growth factors; gene vectors; viral vectors; anti-angiogenesis agents; cytostatic, cytotoxic, and cytocidal agents; transforming agents; apoptosis-inducing agents; radiosensitizers; radioprotectants; hormones; enzymes; antibiotics; antiviral agents; mitogens; cytokines; anti-inflammatory agents; immunotoxins; antibodies; and antigens.

Therapeutically active component 14 is not, however, limited to any of the above-listed compositions or uses. Rather a skilled artisan can select a particular composition of use as the therapeutically active component 14 depending on the application that the brachytherapy seed 10 is intended to be used for. For example, where the seed 10 is intended to be used as a primary treatment for prostate cancer, the therapeutically active substance 14 can include a antineoplastic drug such as paclitaxel (taxol), cisplatin, or 5-fluorouracil; or a hormone such as leuprolide. As another example, where the seed 10 is intended to be used as an adjuvant to radiation treatment for prostate cancer, the therapeutically active substance 14 can include a radiosensitizing agent such as tirapazamine, BUdR, IUdR, or etanidazole. Because brachytherapy seed 10 allows in situ drug delivery to a tissue, the therapeutically active substance 14 might in some cases include a drug that is usually considered too toxic to treat a given condition if given systemically, e.g., tirapazamine or camptothecin.

As indicated in the above description of the brachytherapy seed 10 shown in FIGS. 1 and 2, the biocompatible component 12 is associated with the therapeutically active component 14. As used herein, when referring to the biocompatible component 12 and the therapeutically active component 14, the phrase "associated with" means physically contacting. Thus, in the seed 10, the association of the biocompatible component 12 with the therapeutically active component 14 can take many forms. For example, the biocompatible component 12 and the therapeutically active component 14 can be combined into a mixture as shown in FIGS. 1 and 2. This mixture can have a uniform or non-uniform distribution of components 12 and 14.

The brachytherapy seed 10 shown in FIG. 1 is an example of a uniform mixture of components 12 and 14. The brachytherapy seed 10 of this example can be made by simply mixing together the biocompatible component 12 and the therapeutically active component 14 to form a combination product and then forming the product into the desired size and shape, e.g., using a mold.

Although the brachytherapy seeds shown in FIGS. 1 and 2 include mixture of discrete particles dispersed through a matrix consisting of the therapeutically active component 14, in other versions of brachytherapy seed 10, components 12 and 14 are combined in a single particle or in a larger mass without discrete particles (e.g., a pellet the size and shape of brachytherapy seed 10). For example, biocompatible component 12 and therapeutically active component 14 can be dissolved into a liquid and then dried or cured to form microspheres or a larger pellet made up of a homogeneous distribution of both components 12 and 14. (see, e.g., Ramirez et al., J. Microencapsulation 16:105, 1999). Microspheres can be of any size suitable for use in the invention. For example, they can have a diameter of about 1 to 1000 microns (e.g., 10–100 microns, 100–200 microns, 200–300 microns, 300–400 microns, 400–500 microns, 500–600 microns, 600–700 microns, 700–800 microns, 800–900 microns, 900–1000 microns). The skilled artisan can select the desired size according to the properties desired and particular properties of the microsphere constituents. In one variation of this, the microspheres are also made to include magnetic elements. The microspheres can then be molded or compressed together into the desired shape and sized of brachytherapy seed 10. The larger pellet can likewise be sculpted, extruded, molded or compressed into the desired shape and size of brachytherapy seed 10. Alternatively, the liquid mixture of components 12 and 14 can be poured into a mold defining the shape and size of brachytherapy seed 10, and then cured in the mold. Brachytherapy seeds having components 12 and 14 combined in a single particle or in a larger mass (rather than discrete particles of each) are advantageous for delivering the therapeutically active component 14 into a target tissue over longer time periods.

In other embodiments of seed 10, components 12 and 14 are not necessarily homogeneously mixed in the seed 10. Rather they can be positioned in different areas of the seed 10. For example, components 12 and 14 can separately be fashioned into discrete sections, strips, coils, tubes, etc. The discrete sections, strips, coils, tubes, etc. of the component 12 can then be combined (e.g., by molding together, adhering, structurally interlocking, etc.) with the discrete sections, strips, coils, tubes, etc. of the component 14 to form the seed 10. In another embodiment, the seed 10 shown in FIG. 2 can be modified by filling the cylindrical cavity 20 with a hydrogel (e.g., hydrogels from Alkermes, Cambridge, Mass.) including a therapeutically active substance, and capping off the ends of the hollow tube 18.

Many different therapeutically active substances have been associated with biocompatible materials for use in drug delivery systems apart from brachytherapy seeds. These include, for example, adriamycin (Moritera et al., Invest. Ophthal. Vis. Sci. 33:3125–30, 1992); bupivicaine (Park et al., J. Controlled Release 52:179–189, 1998); camptothecin (Weingart et al., Int. J. Cancer 62:1–5, 1995); carboplatin (Chen et al., Drug Delivery 4:301–11, 1997); carmustine (Brem et al., J. Neurosurg 74:441–6, 1991; and U.S. Pat. Nos. 4,789,724 and 5,179,189); cefazolin (Park et al., J. Controlled Rel. 52:179–189, 1998); cisplatin (Yapp et al., IJROBP 39:497–504, 1997); cortisone (Tamargo et al., J. Neurooncol. 9:131–8, 1990); cyclosporine (Sanchez et al., Drug Delivery 2:21–8, 1995); daunorubicin (Dash et al., J. Pharmacol. Tox. Meth. 40:1–12, 1999); dexamethasone (Reinhard et al., J Contr. Rel. 16:331–340, 1991); dopamine (During et al., Ann. Neurol. 25:351–6, 1989); etanidazole (Yapp et al., Radiotherapy Oncol. 53:77–84, 1999); 5-fluorouracil (Menei et al., Cancer 86:325–30, 1999); fluconazole (Miyamoto et al., Curr. Eye Res. 16:930–5, 1997); 4-hydroxycyclophosphamide (Judy et al., J. Neurosurg. 82:481–6, 1995); ganciclovir (Kunou et al., J. Controlled Rel. 37:143–150, 1995); gentamicin (Laurentin et al., J. Orthopaed. Res. 11:256–62, 1993); heparin (Tamargo et al., J Neurooncol. 9:131–8, 1990); interleukin-12 (Kuriakose et al., Head & Neck 22:57–63, 2000); naproxen (Conforti et al., J. Pharm. Pharmacol. 48:468–73, 1996); nerve growth factor (Camerata et al., Neurosurgery 30:313–19, 1992); retroviral vector producer cells to transfer a cytotoxic gene product (Beer et al., Adv. Drug Deliver. Rev. 27:59–66, 1997); taxol (Park et al., J. Controlled Rel. 52:179–189, 1998; and Harper, E et al., Clin. Cancer Res., 5:4242–4248, 1999); tetanus toxoid (Alonso et al., Vaccine 12:299–306, 1994); tetracaine hydrochloride (Ramirez et al., J. Microencap. 16:105–15, 1999); tirapazamine (Yuan et al., Radiation Oncol. Investig. 7:218–30, 1999); thyrotropin-releasing hormone (Kubek et al., Brain Res. 809:189–97, 1998); and vaccines (Chattaraj et al., J. Controlled Rel. 58:223–32, 1999). Other therapeutically active substances that can be combined with a biocompatible component include: anesthetics, angiogenesis inhibitors (e.g., Lau D. H. et al., Cancer Biother. Radiopharm. 14:31–6,1999), antibiotics (e.g., Bahk J. Y. et al., J. Urol. 163:1560–4, 2000; and Miyamoto H. et al., Current Eye Research 16:930–5, 1997), antibodies (e.g., Gomez S. M. et al., Biotechnol. Prog. 15:238–44, 1999), anticoagulants (e.g., Tamargo R. J. et al., J. Neurooncol. 9:131–138, 1990), antigens (e.g., MachlufM. et al., J. Pharm. Sci. 89:1550–57, 2000), anti-inflammatory agents (e.g., Reinhard C. S. et al., J. Controlled Release 16:331–40, 1991; and Tamargo R. J. et al., J. Neurosurg. 74:956–61, 1991), antivirals, apoptosis-inhibiting agents (e.g., Macias D. et al., Anat. Embryol. (Berl) 193:533–41, 1996), cytokines (e.g., Edelman E. R. et al., Biomaterials 12:619–26, 1991), cytotoxic agents (e.g., Berm H. et al., J. Nueorsurg. 80:283–90, 1994; Berm H. et al., J. Neurosurg. 80:283–90, 1994 Berm H. et al., Lancet 345:1008–12, 1995; Ewend M. G. et al., Cancer Res. 56:5217–23, 1996; Fung L. K. et al., Cancer Res. 58:672–85, 1998; Grossman S. et al., J. Neurosurg. 76:640–47, 1992; Kong Q. et al., J. Surgical Oncology 69:76–82, 1998; Shikani A. H. et al., Laryngoscope 110:907–17, 2000; Straw R. C. et al., J. Orthop. Res. 12:871–7, 1994; Tamargo R. J. et al., Cancer Research 53:329–33, 1993; Valtonen S. et al., Neurosurgery 41:44–9, 1997; Walter K. A. et al., Cancer Research 54:2207–12, 1994; Yapp D. T. T. et al., IJROBP 39:497–504, 1997; Yapp D. T. T. et al., Anti-Cancer Drugs 9:791–796, 1998; Yapp D. T. T. et al., IJROBP 42:413–20, 1998; and Yoshida M. et al., Biomaterials 10:16–22, 1989), enzymes (e.g., Park T. G. et al., J. Control Release 55:181–91, 1998), gene vectors (e.g., Hao T. et al., J. Control Release 69:249–59, 2000; and Maheshwari A. et al., Mol. Ther. 2:121–30, 2000), hormones (e.g., Rosa G. D. et al., J. Control Release 69:283–95, 2000), immunosuppressants (e.g., Sanchez A. et al., Drug Delivery 2:21–8, 1995), mitogens (e.g., Ertl B. et al., J. Drug Target 8:173–84, 2000), neurotransmitters (e.g., During M. J. et al., Ann Neurology 25:351–6, 1989), radioprotectants (e.g., Monig H. et al., Strahlenther Onkol. 166:235–41, 1990), radiosensitizers (e.g., Williams J. A. et al., IJROBP 42:631–39, 1998; and Cardinale R. M. et al., Radiat. Oncol. Invest. 6:63–70, 1998), stimulating and growth factors, transforming agents (e.g., Hong L. et al., Tissue Eng. 6:331–40, 2000), and viral vectors.

The foregoing combination products (i.e., at least one biocompatible component mixed with at least one therapeutically active component) can be used in the brachytherapy seeds of the invention by forming them into a size and shape suitable for passing through the bore of a needle such as one in a conventional brachytherapy seed implantation device.

Referring now to FIGS. 3A–F, in others embodiments of the invention, a brachytherapy seed 10 includes a biocompatible component 12 associated with a therapeutically active component 14, and a radiopaque marker 30 attached to the biocompatible component 12 and/or the therapeutically active component 14. Radiopaque marker 30 allows for the position of brachytherapy seed 10 to be determined using standard X-ray imaging techniques (e.g., fluoroscopy) after seed 10 has been implanted in a target tissue. Proper positioning of seed 10 and spacing of a plurality of brachytherapy seeds in a given target tissue is important for ensuring that the therapeutically active component 14 is delivered adequately to the site of the disease in the target tissue.

Radiopaque marker 30 can be made of any substance that can be detected by conventional X-ray imaging techniques. See, e.g., Fundamentals of Diagnostic Radiology, 2d edition, William E. Brant and Clyde A. Helms (eds.), Lippincott, Williams and Wilkins, 1999; Physical Principles of Medical Imaging, 2d ed., Perry Jr. Sprawls, Medical Physic Publishing, 1995; Elements of Modern X-ray Physics, Jens Als-Nielsen and Des McMorrow, Wiley & Sons, 2001; X-ray and Neutron Reflectivity: Principles and Applications, J. Daillant et al., Springer-Verlag, 1999; Methods of X-ray and Neutron Scattering in Polymer Science, Ryoong-Joon J. Roe, Oxford University Press, 2000; and Principles of Radiographic Imaging: An Art & A Science, Richard R. Carlton, Delmar Publishers, 2000. Many such substances that can be used as marker 30 are known including, most notably, high atomic number (i.e., "high Z") elements or alloys or mixtures containing such elements. Examples of these include platinum, iridium, rhenium, gold, tantalum, bismuth alloys, indium alloys, solder or other alloys, tungsten and silver. Many currently used radiopaque markers that might be adapted for use in the invention include platinum/iridium markers from Draximage, Inc.; and International Brachytherapy; gold rods from Bebig GmbH; gold/copper alloy markers from North American Scientific, palladium rods from Syncor; tungsten markers from Best Industries; silver rods from Nycomed Amersham; silver spheres from International Isotopes Inc, and Urocor, and silver wire from Implant Sciences Corp. Other radiopaque markers include polymers impregnated with various substances (see, e.g., U.S. Pat. Nos. 6,077,880; 6,077,880; and 5,746,998). Radiopaque polymers useful in the invention are described in European Patent Application 894, 503 filed May 8, 1997; European Patent Application 1,016,423 filed Dec. 29, 1999; and published PCT application WO 9605872 filed Aug. 21, 1995. Those radiopaque polymers that are biodegradable are preferred in applications where it is desired to have the implant degrade over time in the implantation site.

Figure 3A:
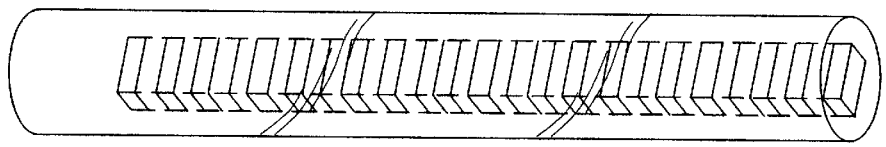
FIGS. 3A–3G are schematic side views of several versions of brachytherapy seeds within the invention that include a radiopaque marker.
Figure 3B:
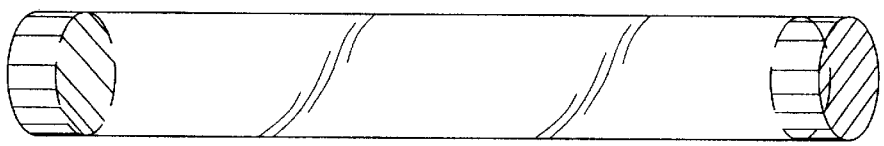
Figure 3C:
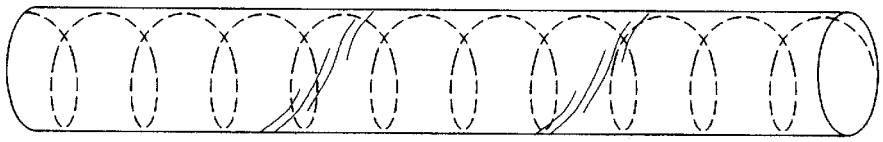
Figure 3D:
Figure 3E:
Figure 3F:
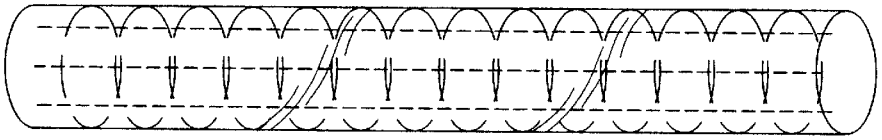
Figure 3G:
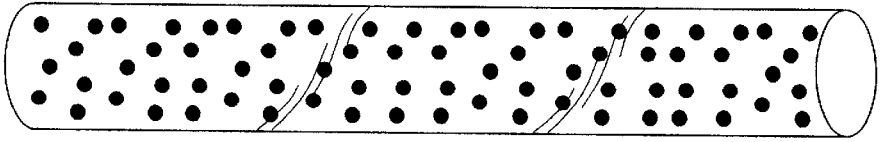

As indicated above, radiopaque marker 30 is attached to seed 10 via the biocompatible component 12 and/or the therapeutically active component 14. The exact manner in which radiopaque marker 30 is attached to seed 10 can is not critical so long as (a) the seed 10 can be passed through the bore of a brachytherapy implantation needle and (b) the attachment allows the position of seed 10 to be readily detected by X-ray imaging. A description of some different examples of how marker 30 can be associated with seed is presented in FIGS. 3A–F. In the embodiment shown in FIG. 3A, the radiopaque marker 30 in the form of a ribbon, filament, strip, thread, or wire is placed in the center and along the length of cylindrical seed 10. In FIG. 3B, the radiopaque marker 30 takes the form of two end caps placed at both ends of cylindrical seed 10. In the embodiment illustrated in FIG. 3C, the radiopaque marker 30 is a coil made of a radiopaque substance running through the length of cylindrical seed 10 as shown. In FIG. 3D, the radiopaque marker 30 takes the form of two beads or pellets placed at two locations along cylindrical seed 10. In the embodiment shown in FIG. 3E, the radiopaque marker 30 takes the form of two bands or rings placed at two locations along the outer surface of cylindrical seed 10. In the seed 10 shown in FIG. 3F, the radiopaque marker 30 takes the form of a mesh formed into cylindrical shape. In the seed 10 shown in FIG. 3G, the radiopaque marker 30 is dispersed throughout the seed in a stippled pattern.

A particularly preferred embodiment of a brachytherapy seeds having a radiopaque marker is one in which the radiopaque markers is a polymer. In one version of this embodiment, such radiopaque polymers are combined with a biocompatible component and a therapeutically active component to form a brachytherapy seed that can be visualized by X-ray imaging. Alternatively, the radiopaque polymer can serve as the biocompatible component. As one example of the former, microspheres made of a radiopaque polymer are co-mingled with microspheres containing a biocompatible component and microspheres containing (e.g., encapsulating) a therapeutically active component (or microspheres containing both a biocompatible component and a therapeutically active component). The co-mingled microspheres are then molded into a radiopaque brachytherapy seed. As another example, the radiopaque polymer, the biocompatible component, and the therapeutically active component can be mixed together into a liquid, and the liquid can be cured to form a solid pellet that can be sculpted, molded, compressed, or otherwise made into the size and shape of a brachytherapy seed. An advantage of preparing a radiopaque brachytherapy seed in this manner is that, after implantation, the entire seed can be visualized by X-ray imaging rather than only a portion of a seed (e.g., as occurs with seeds utilizing conventional markers).

Figure 4A:
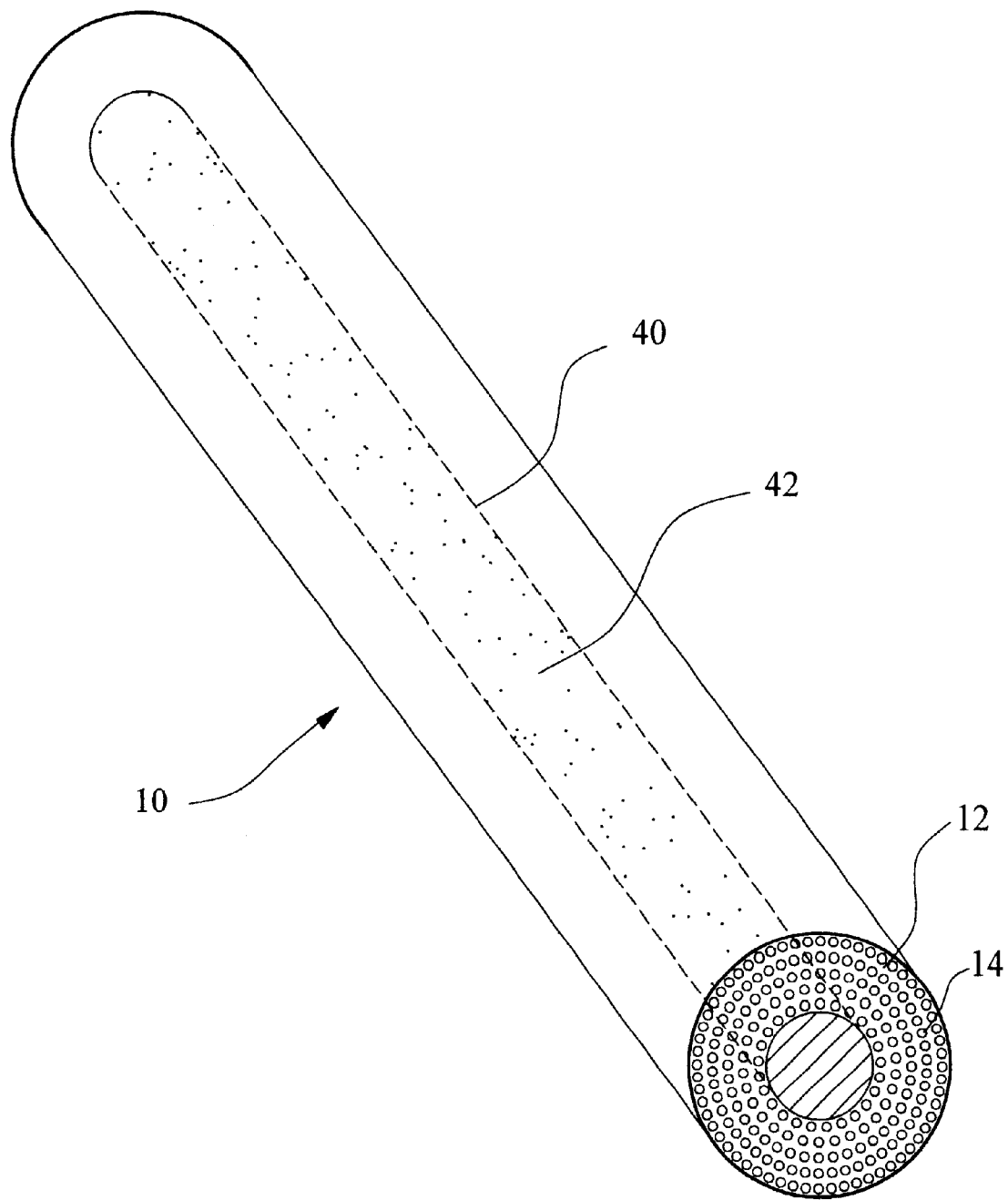
FIG. 4A is a schematic view of a brachytherapy seed of the invention having a sealed container housing a radioisotope partially coated by a therapeutically active component and a biocompatible component.
Figure 4B:
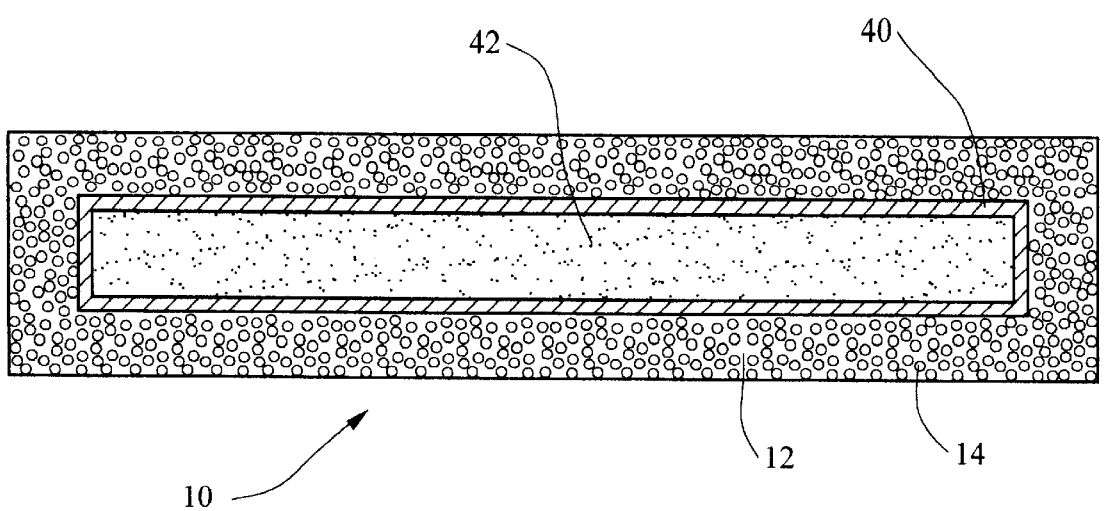
FIG. 4B is a cross-sectional view of a brachytherapy seed of the invention having a sealed container housing a radioisotope completely coated by a therapeutically active component and a biocompatible component.

Referring now to FIGS. 4A and 4B, in another aspect of the invention, a brachytherapy seed 10 includes a biocompatible component 12 associated with a therapeutically active component 14, and a sealed container 40 housing a radioisotope 42. Sealed container 40 is at least partially coated (e.g., partially coated in the version shown in FIG. 4A, and completely coated in the version shown in FIG. 4B) by the biocompatible component 12 and/or the therapeutically active component 14. Sealed container 40 is similar in some respects to those employed in conventional radioactive brachytherapy seeds (e.g., those lacking a biocompatible component 12 associated with a therapeutically active component 14). Thus to prevent leaching of radioisotope 42 after seed 10 is implanted into a target tissue, sealed container 40 is made of a non-biodegradable substance such as titanium or stainless steel. Further, radioisotope 42 is hermetically sealed within container 40.

The exact shape of sealed container 40 is not critical as long as it can be at least partially coated with component 12 and/or 14 to form a brachytherapy seed that can fit through the bore of a brachytherapy implantation needle. It can thus vary in shape from cylindrical (as shown in FIG. 4), cuboid, spheroid, ovoid, ellipsoid, irregularly shaped, etc. Of more importance is the size of sealed container 40. Because the brachytherapy seed 10 containing both the sealed container 40 and the biocompatible component 12 and/or therapeutically active component 14 must fit through the bore of a brachytherapy implantation needle, container 40 must be smaller than the overall size of seed 10. In the example shown in FIG. 4B, sealed container 40 is a cylindrical cannister placed down the center of the length of the rod-shaped seed 10 in a coaxial fashion. Thus, where the seed 10 has a diameter of about 0.8 mm and a length of about 4.5 mm, sealed container will have a diameter less than 0.8 mm (e.g., 0.1, 0.15, 0.2, 0.25, 0.3, 0.35, 0.4, 0.45, 0.5, 0.55, 0.6, 0.65, 0.7, or 0.75 mm) and a length less than 4.5 mm (e.g., 1, 1.5, 2, 2.5, 3, 3.5, or 4 mm). And rather than having only a single sealed container 40 included within brachytherapy seed 10, there can be two or more such containers (e.g., 2, 3, 4, 5, 6, 7, 8, 9, 10 or more) housing the radioisotope 42.

The therapeutically active agent 14 in seed 10 including the sealed container 40 can be any of those agents described above. Preferably, however, the agent 14 is selected to provide a synergistic effect when used in combination with the radioisotope 42 to treat a particular diseased tissue. For example, in this preferred embodiment, agent 14 can be a radiosensitizing agent such as 5- FU, etanidazole, tirapazamine, BUdR, and/or IUdR. Various combinations of substances are known to be more effective when used in combination than when used alone. See, e.g, Brem et al., J. Neurosurg. 80:283–290, 1994; Ewend et al., Cancer Res. 56:5217–5223, 1996; Cardinale, Radiation Oncol. Investig. 6:63–70, 1998; Yapp et al., Radiotherapy and Oncol. 53:77–84, 1999; Yapp, IJROBP 39:497–504, 1997; Yuan et al., Radiation Oncol. Investig. 7:218–230, 1999; and Menei et al., Cancer 86:325–330, 1999.

Radioisotope 42 can be any substance that emits electromagnetic radiation (e.g., gamma-rays or X-rays), beta-particles or alpha-particles and is suitable for use in brachytherapy seed 10. Examples of such substances include those that decay principally by electron capture followed by X-ray emission such as palladium-103 and iodine-125; isotopes that decay by the emission of beta-particles such as gold-198, gold-199, yttrium-90, and phosphorus-32; isotopes that decay with the emission of both beta-particles and gamma-rays such as iridium-192; and isotopes that decay with the emission of alpha-particles such as americium-241. Also useful is gadolinium-157, e..g, for use in boron-neutron capture therapy, and californium-252, rhenium-188, samarium-153, indium-111, and holmium-166. For the treatment of prostate cancer, palladium-103 and iodine-125 are preferred as these have been the subject of much clinical investigation for the treatment of the disease. The amount of radioactivity of radioisotope 42 can vary widely. For example, when using palladium-103 or iodine-125, an exemplary amount to treat prostate cancer about 0.33 mCi and 1.5 mCi per seed if about 50–150 seeds are used at the time of implantation. In other applications the radioactivity per seed can range from about 0.01 mCi to about 100 mCi.

In one embodiment, radioisotope 42 can be mixed with and then configured into microspheres, or it can be encapsulated by the biocompatible component to form microspheres. The radioactive microspheres can be molded or otherwise sized and shaped into a brachytherapy seed suitable for implantation via a brachytherapy implantation device. In one version of this embodiment, the biocompatible component is biodegradable such that the radioisotope contained by this component is gradually released from the seed. Alternatively, the biocompatible component and radioisotope can be mixed together and configured as an amorphous pellet having the size and shape of a brachytherapy seed suitable for implantation via a brachytherapy implantation device.

Figure 5A:
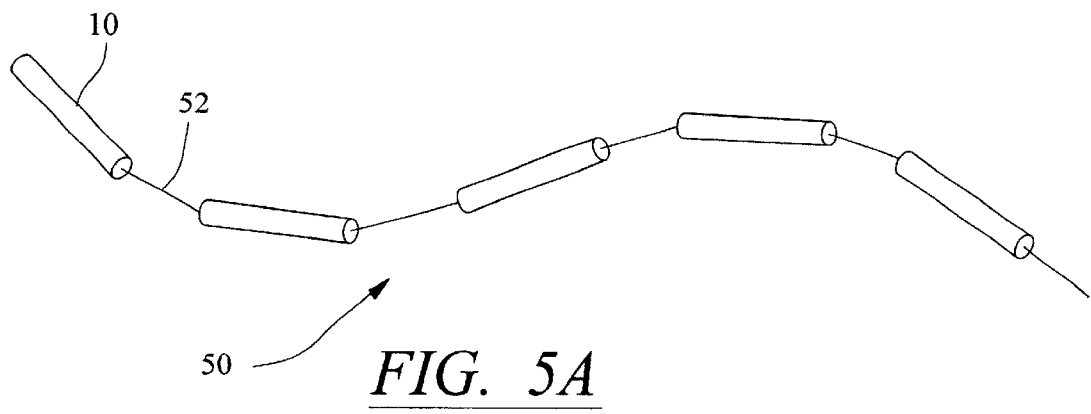
FIG. 5A is a schematic view of a flaccid chain of several brachytherapy seeds conjoined with several spacer elements.
Figure 5B:
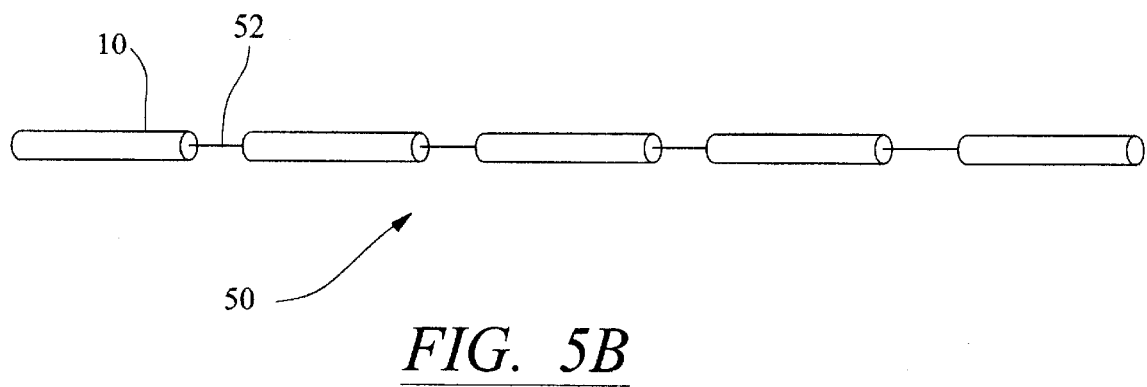
FIG. 5B is a schematic view of a rigid chain of several brachytherapy seeds conjoined with several spacer elements.

In another embodiment of the present invention as illustrated in FIGS. 5A and 5B, a plurality of brachytherapy seeds 10 may be conjoined into a chain 50 using a plurality of spacers 52 to connect the plurality of seeds 10. In the embodiments shown in FIGS. 5A and 5B, a spacer 52 is used to connect two adjacent seeds 10. Spacer 52 can have any size suitable for use with brachytherapy seed 10. And where a plurality of spacers are used in one chain 50, the length of each spacer 52 can be the same or different from the other spacers 52. For many applications the length of spacer 52 will vary from between about 0.5 mm to about 50 mm (e.g., 0.4, 0.5, 1, 2, 3, 4, 5, 5.5, 6, 7, 8, 9, 10, 15, 20, 25, 30, 35, 40, 45, 50, or 51 mm). In many cases, it is important to minimize the bunching or straying of seeds 10 to avoid over- or under-dosing of the target tissue by the therapeutically active component 14 and/or radioisotope 42. Thus, the length of spacer 52 should be selected accordingly.

Spacer 52 can be made of a biocompatible material that can be used to join two brachytherapy seeds. See, e.g., U.S. Pat. No. 6,010,446. The biocompatible material can be either biodegradable or non-biodegradable. For example, spacer 52 can be made of catgut or a like material. Spacers designed for use with conventional radioactive brachytherapy seeds can be used in chain 50. For example, Ethicon, Inc. (Cincinnati, Ohio) manufactures the PG 910 non-sterile autoclavable spacer for Indigo (Cincinnati, Ohio) that is sold in conjunction with an Express Seed Cartridge. In addition, Medical Device Technologies, Inc. (Gainesville, Fla.) distributes a pre-sterilized 5.5 mm long absorbable pre-cut spacer that is made of collagen (Look®, model number 1514b). Materials for use as the spacer 52 are also manufactured by Surgical Specialties Corp. (Reading, Pa.). Where spacer 52 is made of a relatively flexible material, the chain 50 can be relatively flaccid as shown in FIG. 5A. Where spacer 52 is made of an inflexible material, chain 50 will be rigid as shown in FIG. 5B.

In some embodiments of the present invention, the spacer 52 may include a radiopaque substance (e.g., a high Z material or radiopaque polymer described above), so that spacer 52 serves both to facilitate locating an implanted brachytherapy seed by X-ray imaging as well as to physically join together (and/or control the distance between) two or more seeds.

Spacer 52 can be connected to seed 10 by any means known. For example, spacer 52 can be connected to seed 10 by direct attachment such as by gluing, crimping, or melting. Spacer 52 can be attached to any portion of the seed 10. For rod or cylinder-shaped seeds 10, to facilitate implantation, it is generally preferred that spacer 52 be attached to the ends of the seeds 10 that the ends would be adjacent to one another when the chain 50 is inserted into the barrel of a brachytherapy implantation needle. Spacer 52 and seed 10, however, need not be physically attached to each other. Rather they can also be associated with each other by placing each with within the lumen of a tube. The tube can be used to load a brachytherapy seed implantation device with a plurality of spacers 52 and seeds 10 in any sequence. For example, the brachytherapy seed implantation device can be loaded with one (or 2, 3, 4, 5, or more) spacer 52 being interposed between every two seeds 10. Similarly, the brachytherapy seed implantation device can be loaded with one (or 2, 3, 4, 5, or more) seed 10 being interposed between every two spacers 52.

Methods of Making Brachytherapy Seeds

Brachytherapy seeds of the invention can be made by first providing a biocompatible component and a therapeutically active component; then physically associating the two components to form a combination product; and finally forming the combination product into a seed having a size and shape suitable for passing through the bore of a brachytherapy implantation needle (e.g., one having an interior diameter of less than about 2.7 millimeters (10 gauge)). Seeds can be formed into a suitable size and shape by any suitable method, e.g., molding, pressing, extruding, stamping, or chopping.

Brachytherapy seeds of the invention that are associated with a radiopaque marker can be made similarly with the addition of a step of associating the radiopaque marker with the seed. Brachytherapy seeds of the invention that include a sealed container housing a radioisotope can be made by at least partially coating the container with the biocompatible component and therapeutically active component.

Method for Administering a Therapeutically Active Component to a Target Tissue in a Subject The brachytherapy seeds of the invention can be fashioned into a size and shape similar or identical to conventional radioactive brachytherapy seeds. Accordingly, the brachytherapy seeds of the invention can be implanted into a target tissue within a subject (e.g., a human patient or a non-human animal) by adapting known methods for implanting conventional radioactive brachytherapy seeds into a tissue. For example, the brachytherapy seeds of the present invention can be implanted using one or more implantation needles; Henschke, Scott, or Mick applicators; or a Royal Marsden gold grain gun (H. J. Hodt et al., British J. Radiology, pp. 419–421, 1952). A number of suitable implantation devices are described in, e.g., U.S. Pat. Nos. 2,269,963; 4,402,308; 5,860,909; and 6,007,474.

Pharmacokinetics

The brachytherapy seeds of the invention can advantageously be used to selectively deliver a predetermined amount of a therapeutically active substance to a target tissue. For example, when a brachytherapy seed including a therapeutically active substance is implanted in a prostate, the therapeutically active substance will be released from the seed into the tissue surrounding the implantation site. The diffusion or release characteristics of the therapeutically active substance in relation to the target tissue, i.e., the pharmacokinetics of the substance, can be modulated by selecting appropriate biocompatible components included within the seeds, and by varying the concentration of the therapeutically active substance in each seed.

In many applications, to treat a given target tissue with a therapeutic agent it is desirable (or even ideal) to fully saturate the target tissue with the therapeutic agent, while avoiding under- or over-dosing the target tissue. This can be achieved by implanting the brachytherapy seeds of the invention into a target tissue using a brachytherapy implantation device so that, e.g., a precise number of seeds can be implanted in precise locations within the target tissue. By previously calculating the rate of diffusion of the therapeutically active substance under experimental conditions (e.g., using tissue from animal models), an appropriate dosage can be delivered to the target tissue. Because use of brachytherapy implantation devices allows the brachytherapy seeds of the invention to be implanted in any number of different desired locations and/or patterns in a tissue, this method is advantageous over methods where a drug or drug impregnated matrix is simply placed on the surface of a tissue or manually inserted into a surgically dissected tissue.

Other Embodiments

While the above specification contains many specifics, these should not be construed as limitations on the scope of the invention, but rather as examples of preferred embodiments thereof. Many other variations are possible. For example, although the foregoing embodiments describe brachytherapy seeds having a single type of therapeutically active component and/or single type of radioisotope, brachytherapy seeds for use in the methods within the invention can also have a plurality of different therapeutically active agents and/or a plurality of different radioisotopes. Accordingly, the scope of the invention should be determined not by the embodiments illustrated, but by the appended claims and their legal equivalents.

What is claimed is:

1. A method for administering a therapeutically active component to a target tissue in a subject, the method comprising the steps of:

providing a brachytherapy seed comprising a non-metal biocompatible component, a therapeutically active component comprising a non-radioactive drug, and a radiopaque marker, said biocompatible component being (a) physically associated with a therapeutically active component and (b) in contact with said radiopaque marker, wherein said brachytherapy seed has a size and shape suitable for passing through the bore of a needle having an interior diameter of less than about 2.7 millimeters (10 gauge);

providing a brachytherapy implantation instrument comprising at least one brachytherapy implantation needle having a bore having an interior diameter of less than about 2.7 millimeters (10 gauge), and being adapted to accept the brachytherapy seed into the bore of the at least one brachytherapy implantation needle and deliver the accepted implantation device into a target tissue;

introducing the brachytherapy seed into the bore of the at least one implantation needle of the brachytherapy implantation instrument;

introducing at least a portion of the at least one brachytherapy implantation needle into a target tissue in the subject; and actuating the brachytherapy implantation instrument such that the brachytherapy seed is delivered through the bore of the brachytherapy implantation needle into the target tissue.

2. The method of claim 1, wherein the target tissue is a diseased tissue.

3. The method of claim 1, wherein the target tissue is a prostate.

4. The method of claim 1, wherein the biocompatible component and the therapeutically active component are formed into a plurality of microspheres.

5. A method administering a therapeutically active component to a target tissue in a subject, the method comprising the steps of:

provinding a brachytherapy seed comprising a sealed container, and a non-metal biocompatible component, and a therapeutically active component comprising a non-radioactive drug, said biocompatible component being physically associated with the therapeutically active component to form a combination product; and said sealed container being made of a non-biodegradable substance, housing a radioisotope, and being at least partially coated with the combination product, wherein said brachytherapy seed having a size and shape suitable for passing through the bore of a needle having an interior diameter of less than about 2.7 millimeters (10 gauge);

providing a brachytherapy implantation instrument comprising at least one brachytherapy implantation needle having a bore having an interior diameter of less than about 2.7 millimeters (10 gauge), and being adapted to accept the brachytherapy seed into the bore of the at least one brachytherapy implantation needle and deliver the accepted implantation device into a target tissue;

introducing the brachytherapy seed into the bore of the at least one implantation needle of the brachytherapy implantation instrument;

introducing at least a portion of the at least one brachytherapy implantation needle into a target tissue in the subject; and actuating the brachytherapy implantation instrument such that the brachytherapy seed is delivered through the bore of the brachytherapy implantation needle into the target tissue.

6. The method of claim 5, wherein the target tissue is a diseased tissue.

7. The method of claim 5, wherein the target tissue is a prostate.

8. The method of claim 5, wherein the biocompatible component and the therapeutically active component are formed into a plurality of microspheres.

* * * * *